(12) United States Patent
West

(10) Patent No.: US 8,779,349 B2
(45) Date of Patent: Jul. 15, 2014

(54) MINIMIZING AMBIENT LIGHT IN A FEEDBACK CIRCUIT IN PULSE OXIMETER TEST INSTRUMENTS

(75) Inventor: Tom West, Everett, WA (US)

(73) Assignee: Fluke Corporation, Everett, WA (US)

( * ) Notice: Subject to any disclaimer, the term of this patent is extended or adjusted under 35 U.S.C. 154(b) by 580 days.

(21) Appl. No.: 13/043,395

(22) Filed: Mar. 8, 2011

(65) Prior Publication Data

US 2012/0228470 A1    Sep. 13, 2012

(51) Int. Cl.
| | | |
|---|---|---|
| G01J 1/44 | (2006.01) | |
| H01J 5/02 | (2006.01) | |
| A61B 5/00 | (2006.01) | |
| G01J 1/42 | (2006.01) | |
| A61B 5/1495 | (2006.01) | |
| A61B 6/00 | (2006.01) | |

(52) U.S. Cl.
CPC .............. *G01J 1/42* (2013.01); *A61B 5/1495* (2013.01); *A61B 6/582* (2013.01)
USPC ...................... 250/239; 250/214 AL; 600/331

(58) Field of Classification Search
CPC ............. G01J 1/44; G01J 1/42; G01J 1/00; G01J 1/10; G01J 1/18; G01J 5/522; G01J 5/54; G01J 1/0271; G01J 1/4228; G01J 1/08; G01J 1/32; G01J 1/0214; A61B 5/14532; A61B 5/14552; A61B 5/00; A61B 5/1495; A61B 6/58; A61B 6/582; A61B 6/583; G01D 18/00; G01N 21/274

USPC ............ 250/214 AL, 239, 214 R, 214.1, 205, 250/252.1, 267, 265, 256, 214 C; 340/540, 340/600; 356/40, 39, 41, 42; 600/309, 310, 600/344, 473, 476, 475, 477, 323, 331; 73/1.01

See application file for complete search history.

(56) References Cited

U.S. PATENT DOCUMENTS

| | | | |
|---|---|---|---|
| 5,291,884 A * | 3/1994 | Heinemann et al. | 600/322 |
| 5,348,005 A * | 9/1994 | Merrick et al. | 600/330 |
| 5,413,101 A | 5/1995 | Sugiura | |
| 5,784,151 A * | 7/1998 | Miller et al. | 356/41 |
| 6,141,572 A | 10/2000 | Haas | |
| 6,300,728 B1 * | 10/2001 | Blackburn et al. | 315/307 |
| RE39,268 E | 9/2006 | Merrick | |
| 7,346,378 B2 * | 3/2008 | Ruiter | 600/323 |
| 7,630,078 B1 * | 12/2009 | Nabutovsky et al. | 356/392 |
| 8,175,668 B1 * | 5/2012 | Nabutovsky et al. | 600/323 |

* cited by examiner

*Primary Examiner* — Que T Le
*Assistant Examiner* — Jennifer Bennett
(74) *Attorney, Agent, or Firm* — Christensen O'Connor Johnson Kindness PLLC

(57) ABSTRACT

Generally described, one or more embodiments of the present disclosure are directed to pulse oximeter test instruments for testing pulse oximeters. The pulse oximeter test instruments are configured to linearize a relationship between an input signal and an output signal of a light emitting diode (LED). In some embodiments, the linearized relationship may be obtained by minimizing an amount of ambient light detected by a photosensor in a feedback loop. The photosensor may be located in a housing that limits the amount of ambient light that may be detected.

17 Claims, 4 Drawing Sheets

MINIMIZING AMBIENT LIGHT IN A FEEDBACK CIRCUIT IN PULSE OXIMETER TEST INSTRUMENTS

BACKGROUND

Pulse oximeters are non-invasive medical devices configured to determine peripheral oxygen saturation ($SpO_2$). In particular, pulse oximeters measure a ratio of the optical absorption of two forms of hemoglobin, oxyhemoglobin and deoxyhemoglobin, in blood. The amount of absorption of hemoglobin measured in the blood may then be used to determine the peripheral oxygen saturation $SpO_2$.

Pulse oximeters operate on the principle of spectrophotometry, using wavelengths of light to determine the concentration level of oxygen in blood. Typically, pulse oximeters include a clamping probe that clamps around a translucent part of a patient's tissue, such as a finger. One side of the clamping probe includes light emitting diodes (LEDs) for emitting radiation at two distinct wavelengths towards the patient's tissue, and the other side of the clamping probe includes a photodiode aligned with the LEDs to receive the radiation that transmits through the patient's tissue. The amount of radiation for each wavelength that is received by the photodiode is measured.

Pulse oximeters distinguish between pulsating peripheral blood (AC components) and non-pulsating tissue (DC components). A ratio of the AC component of absorbency for each wavelength and the DC component of absorbency at each wavelength is then used to determine the peripheral oxygen saturation $SpO_2$ in the patient's blood using known radiation absorption levels of hemoglobin in blood.

In order to verify a pulse oximeter's operation, pulse oximeter testers have been used to test the quality or reliability of the measurements made by the pulse oximeter.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure an apparatus for testing a pulse oximeter is provided. The apparatus may include a substrate and a housing surrounding a first portion of the substrate such that a second portion extends from the housing. At least a portion of the housing may be opaque. The substrate may include at least one first photosensor located thereon. The at least one first photosensor may be configured to receive a light pulse and convert the light pulse into an electrical signal. The apparatus may further include electronic circuitry configured to receive the electrical signal and to produce an electrical output signal. The apparatus may further include at least one first light emitting diode configured to receive the electrical output signal and generate an optical output signal. The apparatus may further include a second photosensor aligned with a second light emitting diode. The second photosensor and the second light emitting diode may be located within the housing on the first portion of the substrate in a manner that limits ambient light sensed by the second photosensor. The second light emitting diode may be electrically coupled to the at least one first light emitting diode such that an optical output generated by the second light emitting diode is representative of the optical output signal generated by the at least one first light emitting diode.

In accordance with aspects of the present disclosure a system for testing a pulse oximeter is provided. The system may include a simulation sensor and a simulation controller coupled to the simulation sensor. The simulation sensor may include a substrate and a housing surrounding a first portion of the substrate such that a second portion extends from the housing. At least a portion of the housing may be opaque. The simulation sensor may further include a plurality of first photosensors located on the second portion of the substrate. The plurality of photosensors may be configured to receive light pulses and convert the light pulses into corresponding electrical signals. The simulation sensor may further include electronic circuitry configured to receive the electrical signals and to produce electrical output signals. The simulation sensor may further include a plurality of light emitting diodes configured to receive the electrical output signals and generate optical output signals. The simulation sensor may further include a second photosensor aligned with one of the plurality of light emitting diodes. The second photosensor and the one of the plurality of light emitting diodes may be located within the housing on the first portion of the substrate in a location that limits ambient light from being sensed by the second photosensor. The simulated controller may be configured to control the electronic circuitry in response to various input parameters to produce the corresponding electrical output signals.

In accordance with aspects of the present disclosure an apparatus for testing a pulse oximeter is provided. The apparatus may include a substrate and at least one first photosensor located on the substrate. The at least one first photosensor may be configured to receive a light pulse and convert the light pulse into an electrical signal. The electronic circuitry may be configured to receive the electrical signal and to produce an electrical output signal. The apparatus may further include at least one first light emitting diode configured to receive the electrical output signal and generate an optical output signal. The apparatus may further include a second photosensor aligned with a second light emitting diode. The second photosensor and the second light emitting diode may be located within an opaque housing on the substrate in a manner that limits ambient light sensed by the second photosensor. The second light emitting diode may be electrically coupled to the at least one first light emitting diode such that an optical output generated by the second light emitting diode is representative of the optical output signal generated by the at least one first light emitting diode.

DESCRIPTION OF THE DRAWINGS

The foregoing aspects and many of the attendant advantages of this disclosure will become more readily appreciated or better understood by reference to the following detailed description, when taken in conjunction with the accompanying drawings, wherein.

DETAILED DESCRIPTION

While illustrative embodiments are described below, it will be appreciated that various changes can be made therein without departing from the spirit and scope of the invention. In that regard, the detailed description set forth below, in connection with the appended drawings where like numerals reference like elements, is intended only as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

The following discussion provides examples of pulse oximeter test instruments that may be used to test the quality or reliability of a pulse oximeter. As will be explained below, examples of the pulse oximeter test instruments include a simulation sensor for simulating a patient's tissue, such as the patient's finger. In that regard, the simulation sensor may take the shape of a patient's finger such that a standard clamping probe of a pulse oximeter may be configured to clamp around a portion of the simulation sensor or may take other shapes that can suitably interface with presently available and future developed pulse oximeters. Generally described, the pulse oximeter test instruments described herein aim to linearize a relationship between an input signal and an output signal of a light emitting diode (LED). In some embodiments, the linearized relationship may be obtained by minimizing an amount of ambient light detected by a photosensor in a feedback loop.

Although the pulse oximeter test instruments may be shown and described in reference to a simulated finger sensor, it should be appreciated that any simulation sensor may be used with the pulse oximeter test instruments described herein. In that regard, a simulation sensor may be used to simulate any tissue that may be used with a pulse oximeter, such as a patient's earlobe, toe, or the like.

Figure 1:
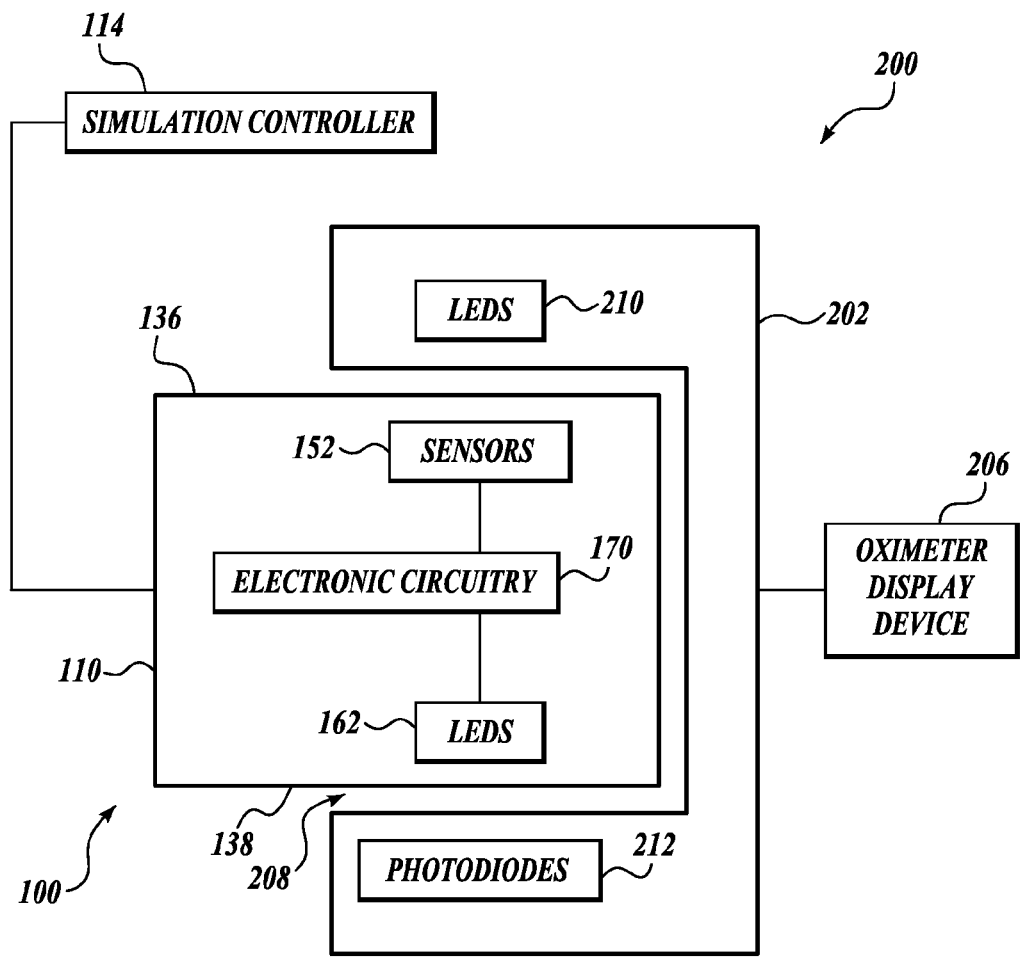
FIG. 1 is a block diagram of one example of a pulse oximeter test instrument associated with a pulse oximeter in accordance with aspects of the present disclosure.
Figure 2:
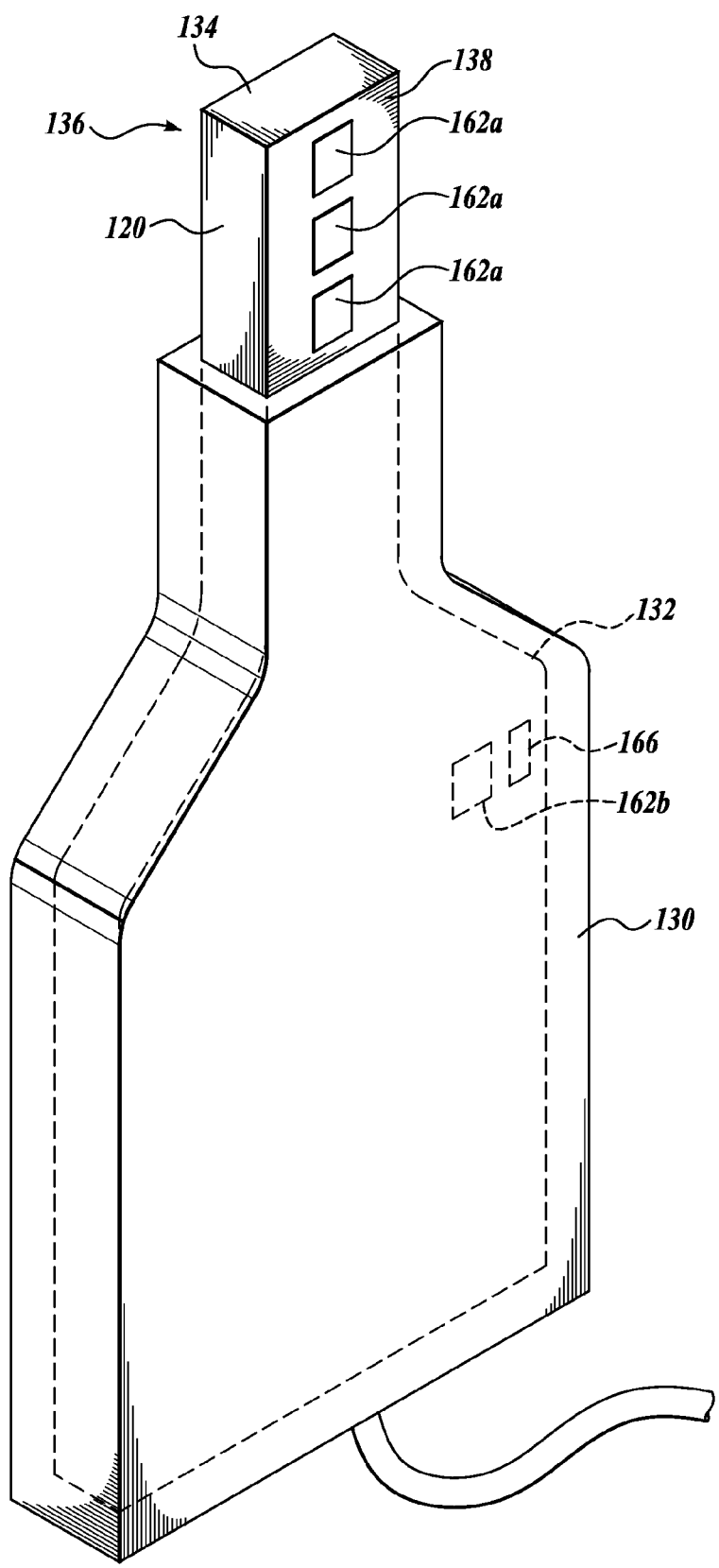
FIG. 2 is an isometric view of a schematic illustration of a pulse oximeter test instrument in accordance with aspects of the present disclosure.

Turning now to FIGS. 1 and 2, there is shown a pulse oximeter test instrument 100 in accordance with aspects of the present disclosure. As will be explained in more detail below, the pulse oximeter test instrument 100 is configured to test an operation of a medical device, such as a pulse oximeter 200 as shown in FIG. 1. In use, the pulse oximeter test instrument 100 is associated with a component, such as a clamping probe 202, of the pulse oximeter 200. In the illustrated embodiment, the pulse oximeter test instrument 100 includes a simulation sensor 110, such as a simulated finger sensor, electrically coupled to a simulation controller 114. In some embodiments, the simulation controller 114 may be integral with the simulation sensor 110. Generally described, the simulation sensor 110 may be configured to simulate a patient's tissue, such as a patient's finger, to test the operation of the pulse oximeter 200. In that regard, the simulation sensor 110 may be configured to simulate absorption of radiation emitted from the pulse oximeter 200 in response to variations in parameters representative of tissue, such as size, color, shape, mass, density, etc., and of blood flow in such tissue. The simulation controller 114 may be configured to adjust various components within the simulation sensor 110 to simulate the various parameters during testing of the pulse oximeter 200.

In the illustrated embodiment and as briefly mentioned above, the pulse oximeter 200 includes a clamping probe 202 coupled to an oximeter display device 206, as is best shown in FIG. 1. The clamping probe 202 includes an opening 208 for receiving a patient's tissue, such as the patient's finger, during normal operation of the pulse oximeter 200. As will be explained in more detail below, a portion of the simulation sensor 110 is suitably sized and shaped to be received within the opening 208 of the clamping probe 202. It should be appreciated that the clamping probe 202 includes suitable structure configured to clamp onto the simulation sensor 110 or the patient's tissue, such as a patient's finger.

Still referring to FIG. 1, one side of the clamping probe 202 includes LEDs 210 on one side facing one or more photosensors, such as photodiodes 212, located on the other side of the clamping probe 202. The one or more photodiodes 212 are configured to receive the light emitted from the LEDs 210 and convert the received optical signals into electrical signals. One or more of the LEDs 210 emits red light, in this example, having a wavelength of about 660 nanometers (nm), and one or more LEDs 210 emit infrared (IR) light having a wavelength of about 940 nm.

Turning to FIG. 2, the simulation sensor 110 includes a substrate 120, such as a printed circuit board (PCB), partially surrounded by a housing 130. It will be appreciated that the substrate 120 may be of any material sufficient to support a plurality of electrical and optical components mounted thereon. The electrical and optical components mounted on the substrate 120 may be coupled together by traces formed within the substrate 120 as is well known in the art. The housing 130 is made of an insulative material and is generally opaque. That is, the housing 130 is generally made from a material that does not allow light to pass therethrough.

In the embodiment shown, the housing 130 surrounds a first portion 132 of the substrate 120 such that a second portion 134 of the substrate 120 extends from the housing 130. The second portion 134 of the substrate 120 that extends from the housing 130 may be of a size and shape to simulate a patient's tissue, such as a finger. In this regard, the second portion 134 may be suitably configured to be inserted into the opening 208 of the clamping probe 202 of the pulse oximeter 200, as is best illustrated in FIG. 1.

The second portion 134 of the substrate 120 includes a plurality of LEDs 162a provided on a first surface 138. Although three LEDs 162a are shown in the illustrated embodiment, it is to be understood that any number of LEDs may be used, including one LED. The first portion 132 of the substrate 120 includes at least one LED 162b. The location of the LED 162b may be in any position on the first portion 132 of the substrate 120 such that the housing 130 surrounds the LED 162b. As will be explained in more detail below, the housing 130 is configured to minimize the amount of ambient light detected by the LED 162b.

A second surface 136 opposite the first surface 138 may include a plurality of photosensors 152, such as photodiodes, mounted on the second portion 134 as is best illustrated in FIG. 1. The photosensors 152 are suitably positioned such that when the simulation sensor 110 is inserted into the opening 208 of the clamping probe 202 of the pulse oximeter 200, the photodiodes 152 of the simulation sensor 110 are aligned with the LEDs 210 of the clamping probe 202, and the LEDs 162 of the simulation sensor 110 are aligned with the photodiodes 212 of the clamping probe 202, as best illustrated by FIG. 1. In that regard, the sensors 152 of the simulation sensor 110 are configured to receive light emitted from the LEDs 210 of the clamping probe 202, and the LEDs 162 of the simulation sensor 110 are configured to emit light to the photodiodes 212 of the clamping probe 202.

In operation, the light detected by the photosensors 152 of the pulse oximeter test instrument 100 is converted to electrical signals and processed by the electronic circuitry 170 as specified by the simulation controller 114. For a description of circuitry that may be included or otherwise associated with the electronic circuitry 170, please see U.S. Pat. No. RE39,268 to Merrick et al., which is herein incorporated by reference for all purposes.

Figure 3:
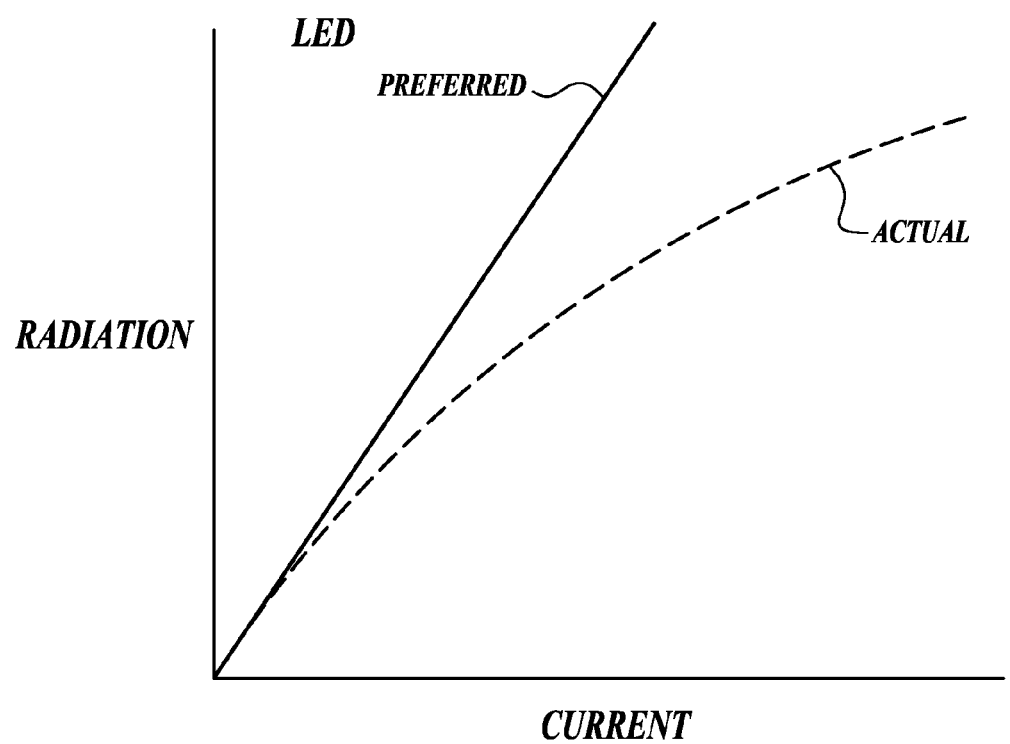
FIG. 3 is a graph illustrating a relationship between an electrical input signal and an optical output signal of a typical LED.

Once processed, appropriate signals are then provided to the LEDs 162 and converted to optical signals. That is, the LEDs 162 are configured to receive an electrical input signal, such as current or voltage, from the electronic circuitry 170 and convert the electrical input signal to an optical output signal for emitting to the photodiodes 212 of the pulse oximeter 200. In general and as illustrated by the curved line labeled "actual" in FIG. 3, the LEDs do not typically produce a linear relationship between the electrical input signal and the optical output signal. That is, as the electrical input signal, such as current, increases, the amount of light generated by the LEDs 162 as the optical output signal does not necessarily increase by a proportional amount. In order to provide adequate control over the pulse oximeter test instrument 100, however, it is preferred to generate an optical output signal that is directly proportional to the electrical input signal as illustrated by the straight line labeled "preferred."

Figure 4:
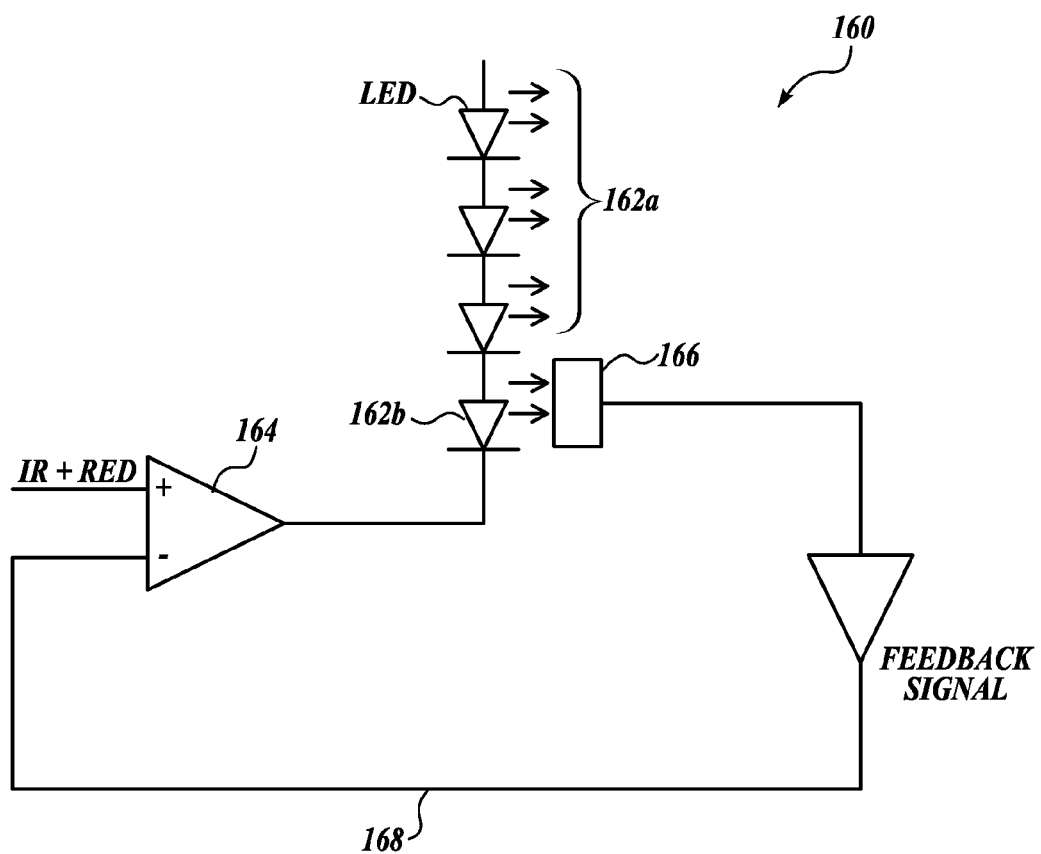
FIG. 4 is a circuit diagram of one example of a light emitting system of a pulse oximeter test instrument in accordance with aspects of the present disclosure.

To produce a linear relationship between the electrical input signal and the optical output signal of the LEDs 162, a feedback signal may be generated. The feedback signal may be used to adjust the optical output signal of the LEDs 162. FIG. 4 illustrates a feedback circuit 160 for a feedback signal in accordance with the present disclosure. The feedback circuit 160 includes an amplifier 164 coupled to a plurality of LEDs 162a and LED 162b. Each of the LEDs 162a and 162b are coupled to one another in series. As discussed above and shown in FIGS. 1 and 2, the LEDs 162a are positioned on the second portion 134 of the substrate 120 and configured to emit optical signals to the photodiodes 212 of the pulse oximeter 200, and the LED 162b is located on the first portion 132 of the substrate 120 and is surrounded by the housing 130. A photosensor 166, such as a photodiode, is aligned with the LED 162b and is configured to sense optical signals emitted from the LED 162b. An output of the photosensor 166 is coupled to an input of the amplifier 164 via a feedback loop 168. As will be explained below, the feedback loop 168 is configured to couple a feedback signal generated by the photosensor 166.

An operation of one embodiment of the feedback circuit diagram 160 will now be described. The amplifier 164 receives an electrical input signal, such as a summed IR and red signal, from the electronic circuitry 170 and the feedback signal from the feedback loop 168 generated by the photosensor 166. As is illustrated by the amplifier 164 in FIG. 4, the amplifier 164 may be configured to invert the received feedback signal to obtain a difference between the feedback signal and the electrical input signal. It should be understood, however, that either one of the IR and red signal or the feedback signal may be inverted to obtain the difference. The inverted feedback signal is now negative and the IR and red signal is positive. If the difference between the inverted feedback signal and the IR and red signal 172 is zero, the LEDs 162 are behaving linearly. If however, the difference is a value other than zero, the electrical signal, such as current, provided to the LEDs 162a and 162b may be adjusted to obtain a linearized relationship between the electrical input signal and the optical output signal.

It should be understood, however, that if the photosensor 166 receives some ambient light along with the optical light emitted from the LED 162b, the feedback signal may be affected by the ambient light. The ambient light may distort the feedback signal thereby causing a non-linearized relationship between the electrical input signal and the optical output signal of the LEDs 162 even after an adjustment has been made. To prevent ambient light from being detected by the photosensor 166, the LED 162b and the photosensor 166 are located within the housing 130 as is illustrated in FIG. 2. As indicated above, the housing 130 is opaque, preventing light from passing therethrough. Therefore, by locating the LED 162b and the photosensor 166 within the housing the amount of ambient light entering the photosensor 166 may be minimized, thus preserving the utility of the feedback circuit 160 to help linearize the optical output signal of the LEDs 162. In another embodiment, a portion of the housing may be opaque. That is, the portion of the housing 130 that surrounds the LED 162b and the photosensor 166 may be opaque, while other portions of the housing 130 are translucent. In yet another embodiment, the LED 162b and the photosensor 166 may be covered by an opaque body that is distinct from the housing 130.

Various principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the claimed subject matter.

The invention claimed is:

1. An apparatus for testing a pulse oximeter, the apparatus comprising:
  a substrate;
  a housing surrounding a first portion of the substrate such that a second portion of the substrate extends from the housing, wherein at least a portion of the housing is opaque;
  at least one first photosensor located on the second portion of the substrate, wherein the at least one first photosensor is configured to receive a light pulse and convert the light pulse into an electrical signal;
  electronic circuitry configured to receive the electrical signal and to produce an electrical output signal;
  at least one first light emitting diode located on the second portion of the substrate that extends from the housing, wherein the at least one first light emitting diode is configured to receive the electrical output signal and generate an optical output signal; and
  a second photosensor aligned with a second light emitting diode, wherein the second photosensor and the second light emitting diode are surrounded by the opaque portion of the housing on the first portion of the substrate such that the opaque portion of the housing separates the second light emitting diode from the at least one first light emitting diode and prevents ambient light from being sensed by the second photosensor,
  wherein the second light emitting diode is electrically coupled in series to the at least one first light emitting diode such that an optical output generated by the second light emitting diode is representative of the optical output signal generated by the at least one first light emitting diode.

2. The apparatus of claim 1, wherein the electrical output signal is a first electrical output signal, and wherein the second photosensor is configured to generate a second electrical output signal that is a feedback signal.

3. The apparatus of claim 2, further comprising circuitry configured to receive the first electrical output signal and the feedback signal and to generate an adjusted electrical output signal based on the feedback signal and first electrical output signal.

4. The apparatus of claim 3, wherein the adjusted electrical output signal is adjusted based on a difference between the feedback signal and the first electrical output signal.

5. The apparatus of claim 1, wherein the at least one first light emitting diode comprises a plurality of first light emitting diodes, and wherein the plurality of first light emitting diodes and the second light emitting diode are coupled in series.

6. The apparatus of claim 1, wherein the at least one photosensor and the second photosensor are photodiodes.

7. The apparatus of claim 1, wherein the entire housing is opaque.

8. A system for testing a pulse oximeter, the system comprising:
a simulation sensor comprising:
   a substrate;
   a housing surrounding a first portion of the substrate such that a second portion of the substrate extends from the housing, wherein at least a portion of the housing is opaque;
   a plurality of first photosensors located on the second portion of the substrate, wherein the plurality of photosensors is configured to receive light pulses and convert the light pulses into corresponding electrical signals;
   electronic circuitry configured to receive the electrical signals and to produce corresponding electrical output signals;
   a plurality of light emitting diodes electrically coupled in series, wherein the plurality of light emitting diodes are configured to receive the corresponding electrical output signals and generate optical output signals; and
   a second photosensor aligned with one of the plurality of light emitting diodes, wherein the second photosensor and the one of the plurality of light emitting diodes are surrounded by the opaque portion of the housing on the first portion of the substrate such that the opaque portion of the housing separates the one of the plurality of light emitting diodes from the other of the plurality of light emitting diodes and prevents ambient light from being sensed by the second photosensor; and
a simulation controller coupled to the simulation sensor, wherein the simulation controller is configured to control the electronic circuitry in response to various input parameters to produce the corresponding electrical output signals.

9. The apparatus of claim 8, wherein the electrical output signals are first electrical output signals, and wherein the second photosensor is configured to generate a second electrical output signal that is a feedback signal.

10. The apparatus of claim 9, further comprising an amplifier configured to receive the first electrical output signals and the feedback signal and to generate an adjusted electrical output signal based on the feedback signal and first electrical output signals.

11. The apparatus of claim 10, wherein the adjusted electrical output signal is adjusted based on a difference between the feedback signal and the first electrical output signals.

12. The apparatus of claim 8, wherein the plurality of first photosensors and the second photosensor are photodiodes.

13. The apparatus of claim 8, wherein the entire housing is opaque.

14. An apparatus for testing a pulse oximeter, the apparatus comprising:
a substrate;
at least one first photosensor located on the substrate, wherein the at least one first photosensor is configured to receive a light pulse and convert the light pulse into an electrical signal;
electronic circuitry configured to receive the electrical signal and to produce an electrical output signal;
at least one first light emitting diode configured to receive the electrical output signal and generate an optical output signal; and
a second photosensor aligned with a second light emitting diode, wherein the second photosensor and the second light emitting diode are surrounded by an opaque housing on the substrate such that the opaque housing separates the second light emitting diode from the at least one first light emitting diode and prevents ambient light from being sensed by the second photosensor,
wherein the second light emitting diode is electrically coupled in series to the at least one first light emitting diode such that an optical output generated by the second light emitting diode is representative of the optical output signal generated by the at least one first light emitting diode.

15. The apparatus of claim 14, wherein the electrical output signal is a first electrical output signal, and wherein the second photosensor is configured to generate a second electrical output signal that is a feedback signal.

16. The apparatus of claim 15, further comprising circuitry configured to receive the first electrical output signal and the feedback signal and to generate an adjusted electrical output signal based on the feedback signal and first electrical output signal.

17. The apparatus of claim 16, wherein the adjusted electrical output signal is adjusted based on a difference between the feedback signal and the first electrical output signal.

* * * * *